United States Patent [19]

Costantini et al.

[11] Patent Number: 5,714,641
[45] Date of Patent: *Feb. 3, 1998

[54] HYDROXYLATION OF PHENOLIC COMPOUNDS

[75] Inventors: Michel Costantini; Adrien Dromard, both of Lyons, France; Michel Jouffret, London, Great Britain

[73] Assignee: Rhone-Poulenc Chimie, Courbevoie Cedex, France

[*] Notice: The term of this patent shall not extend beyond the expiration date of Pat. No. 5,434,317.

[21] Appl. No.: 466,137

[22] Filed: Jun. 6, 1995

Related U.S. Application Data

[63] Continuation of Ser. No. 164,828, Dec. 9, 1993, Pat. No. 5,434,317, which is a continuation of Ser. No. 773,072, Oct. 8, 1991, abandoned.

[30] Foreign Application Priority Data

Oct. 8, 1990 [FR] France ................... 90 12345

[51] Int. Cl.$^6$ .................................. C07C 37/08
[52] U.S. Cl. .......................... 568/768; 568/771
[58] Field of Search ........................ 568/768, 771

[56] References Cited

U.S. PATENT DOCUMENTS 3,849,502 11/1974 Bourdin et al. .
4,078,006 3/1978 Umemura et al. .

FOREIGN PATENT DOCUMENTS 2266683 10/1975 France .
2266684 10/1975 France .

*Primary Examiner*—Rebecca Cook
*Attorney, Agent, or Firm*—Burns, Doane, Swecker & Mathis, L.L.P.

[57] ABSTRACT

Phenolic compounds, e.g., phenol, are hydroxylated, preponderantly into the para-isomer, e.g., hydroquinone, by reaction with hydrogen peroxide in the presence of an effective amount of a strong acid and a catalytically effective amount of a keto compound having the formula (II):

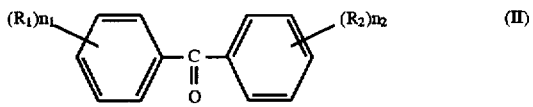

in which $R_1$ and $R_2$, which may be identical or different, are each a hydrogen atom or an electron-donating group; $n_1$ and $n_2$, which may be identical or different, are numbers equal to 0, 1, 2 or 3, with the proviso that the two carbon atoms located at the α-position with respect to the two carbon atoms bearing the —CO group may be bonded together via a valence bond or via a —CH$_2$— group, thereby forming a keto-containing ring member which may either be saturated or unsaturated.

34 Claims, No Drawings

HYDROXYLATION OF PHENOLIC COMPOUNDS

This application is a continuation of application Ser. No. 08/164,828, filed Dec. 9, 1993, U.S. Pat. No. 5,434,317 which is a continuation of application Ser. No. 07/773,072, filed Oct. 8, 1991 abandoned.

BACKGROUND OF THE INVENTION

1. Field of the Invention

The present invention relates to the hydroxylation of phenolic compounds, and, more especially, to the hydroxylation of phenols and phenol ethers with hydrogen peroxide.

2. Description of the Prior Art

Numerous processes for the hydroxylation of phenols are known to this art.

FR-A 2,071,464, in particular, describes a significant industrial process for the hydroxylation of phenols and phenol ethers.

This process entails carrying out the hydroxylation with hydrogen peroxide in the presence of a strong acid. Among these strong acids, sulfuric acid, para-toluenesulfonic acid and perchloric acid are the most widely used.

The hydroxylation of phenol under the conditions described produces a mixture of hydroquinone and pyrocatechol, with a preponderance of the latter, since the hydroquinone/pyrocatechol ratio typically ranges from 0.3 to 0.7.

FR-A 2,266,683 relates to an improvement in the above process, by conducting the hydroxylation in the presence of a ketone. This improves the yield of the reaction with respect to hydroquinone and pyrocatechol. However, in all of the examples, a larger amount of pyrocatechol is produced relative to that of hydroquinone.

The known processes, hence, principally produce pyrocatechol.

Thus, to meet the demand of the commercial market, which fluctuates, need exists for an industrial process that produces hydroquinone as a preponderant final product.

SUMMARY OF THE INVENTION

Accordingly, a major object of the present invention is the provision of an improved process for the hydroxylation of phenol wherein the amount of hydroquinone produced is increased relative to the amount of pyrocatechol.

Another object of the present invention is the provision of an improved process for the hydroxylation of phenol whereby more hydroquinone than pyrocatechol is produced.

Briefly, the present invention features a process for the hydroxylation of phenolic compounds of the formula (I):

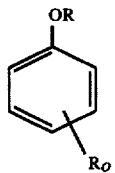
(I)

in which R and $R_0$, which may be identical or different, are each a hydrogen atom, an alkyl radical having from 1 to 4 carbon atoms, a cyclohexyl radical or a phenyl radical, by reacting such phenols with hydrogen peroxide in the presence of an effective amount of a strong acid and a keto compound having the formula (II):

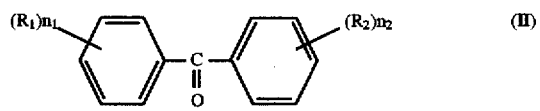
(II)

in which $R_1$ and $R_2$, which may be identical or different, are each a hydrogen atom or an electron-donating group; $n_1$ and $n_2$, which may be identical or different, are numbers equal to 0, 1, 2 or 3, with the proviso that the two carbon atoms located at the α-position with respect to the two carbon atoms bearing the —CO— group may be bonded together via a valence bond or via a —$CH_2$— group, thereby forming a keto-containing ring member which may either be saturated or unsaturated.

DETAILED DESCRIPTION OF THE PREFERRED EMBODIMENTS OF THE INVENTION

More particularly according to the present invention, by the term "electron-donating group" is intended a group as defined by H. C. Brown in the text by Jerry March, *Advanced Organic Chemistry*, chapter 9, pages 243 and 244.

According to the subject process, an electron-donating group is selected which does not react under the acidity conditions of the invention.

Exemplary electron-donating groups which are suitable for the present invention include:

(i) linear or branched alkyl radicals having from 1 to 4 carbon atoms, (ii) the phenyl radical, (iii) alkoxy radicals $R_3$—O—, in which $R_3$ is a linear or branched alkyl radical having from 1 to 4 carbon atoms or a phenyl radical, (iv) the hydroxyl group, (v) the fluorine atom.

It has now unexpectedly been found that the presence of a keto compound corresponding specifically to the formula (II) during the hydroxylation of phenol with hydrogen peroxide exerts an influence on the selectivity with respect to the formation of the hydroquinone, increasing the production of this compound at the expense of pyrocatechol.

Thus, certain of the compounds indicated above permit the hydroquinone/pyrocatechol mole ratio to be increased from a value less than 1.0 to a value greater than or equal to 1.0. Particularly representative such keto compounds are those corresponding to the general formula (II) in which $R_1$ and $R_2$, which may be identical or different, are each a hydrogen atom or an electron-donating group, preferably at the 4,4'-position, and $n_1$ and $n_2$, which may be identical or different, are equal to 0 or 1.

Preferred are the keto compounds corresponding to the formula (II) in which $R_1$ and $R_2$, which may be identical or different, are each a hydrogen atom; a methyl, ethyl, tert-butyl or phenyl radical; a methoxy or ethoxy radical; or a hydroxyl group, preferably at the 3,3'- or 4,4'-position.

Particularly exemplary such ketones include:

Benzophenone,
2-Methylbenzophenone,
2,4-Dimethylbenzophenone,
4,4'-Dimethylbenzophenone,
2,2'-Dimethylbenzophenone,
4,4'-Dimethoxybenzophenone,
Fluorenone,
4-Hydroxybenzophenone, 4,4'-Dihydroxybenzophenone,
4-Benzoylbiphenyl.

According to the present invention, the presence of the keto compound of formula (II) during the hydroxylation of the phenolic compound of formula (I) influences the regioselectivity of the reaction.

Such keto compound is employed in a catalytically effective amount. In general, the amount of the keto compound of formula (II), expressed in moles per mole of hydrogen peroxide, ranges from $1 \times 10^{-3}$ mole to 10. It is unnecessary to exceed 1.0 mole of keto compound per mole of hydrogen peroxide. In practice, the amount of keto compound typically ranges from 0.05 to 1.0 mole per mole of hydrogen peroxide.

The hydrogen peroxide employed can be in the form of an aqueous solution or an organic solution.

Since they are more readily commercially available, aqueous solutions are preferably used.

Although not critical per se, the concentration of the aqueous hydrogen peroxide solution is selected such as to introduce as little water as possible into the reaction medium. An aqueous hydrogen peroxide solution containing at least 20% by weight of $H_2O_2$, and preferably in the region of 70%, is generally used.

The amount of hydrogen peroxide can range up to 1 mole of $H_2O_2$ per mole of phenolic compound of formula (I).

It is, however, preferable, for providing an industrially acceptable yield, to use a mole ratio of hydrogen peroxide to phenolic compound of formula (I) of from 0.01 to 0.3, and preferably from 0.05 to 0.10.

In order to provide a sufficient reaction rate, the initial water content of the medium is limited to 20% by weight, and preferably up to 10% by weight.

The indicated weight contents are expressed relative to the phenolic compound of formula (I)/hydrogen peroxide/water mixture.

This initial water corresponds to the water introduced with the reactants, and in particular with the hydrogen peroxide.

A strong acid participates in the process of the invention. By "strong" acid is intended an acid possessing a pKa in water of less than $-0.1$, and preferably less than $-1.0$.

The pKa is defined as the ionic dissociation constant of the acid/base system when water is used as a solvent.

Among the acids corresponding to this definition, it is preferable to use those which are stable with respect to oxidation by hydrogen peroxide.

Particularly exemplary are the oxoacids, halogenated or otherwise, such as sulfuric acid, pyrosulfuric acid, perchloric acid, nitric acid, halosulfonic acids such as fluorosulfonic acid, chlorosulfonic acid or trifluoromethanesulfonic acid, methanesulfonic acid, ethanesulfonic acid, ethanedisulfonic acid, benzenesulfonic acid, benzenedisulfonic acids, toluenesulfonic acids, naphthalenesulfonic acids and naphthalenedisulfonic acids.

Among such acids, perchloric acid, trifluoromethanesulfonic acid, para-toluenesulfonic acid, chlorosulfonic acid, fluorosulfonic acid and methanesulfonic acid are the preferred.

Perchloric acid and trifluoromethanesulfonic acid are the most preferred.

The amount of acid, expressed as the ratio of the number of equivalents of protons to the number of moles of hydrogen peroxide, can range from about $1 \times 10^{-4}$ to about 1.0.

In a preferred embodiment of the invention, the ratio $H^+/H_2O_2$ ranges from $1 \times 10^{-3}$ to 0.1.

In another preferred embodiment of the invention, an agent which complexes the metal ions present in the medium is added thereto, since the latter exert a deleterious effect on the progress of the process, in particular in the case of phenols where the yields of hydroxylation products are low. Consequently, it is preferable to inhibit the action of these metal ions.

The metal ions which adversely affect the progress of the hydroxylation are transition metal ions, and more especially iron, copper, chromium, cobalt, manganese and vanadium ions.

The metal ions are introduced by the reactants, and in particular the aromatic compounds, and the apparatus used. To inhibit the action of these metal ions, it suffices to conduct the reaction in the presence of one or more complexing agents which are stable with respect to hydrogen peroxide and form complexes which cannot be decomposed by the strong acids present, and in which the metal can no longer exert chemical activity.

Particularly exemplary such complexing agents, include the various phosphoric acids such as, for example, orthophosphoric acid, metaphosphoric acid, pyrophosphoric acid, polyphosphoric acids and phosphonic acids such as (1-hydroxyethylidene)diphosphonic acid, phosphonic acid, ethylphosphonic acid and phenylphosphonic acid.

It is also possible to use the esters of the abovementioned acids. Particularly exemplary thereof are the mono- or dialkyl, mono- or dicycloalkyl and mono- or dialkylaryl orthophosphates, for example ethyl or diethyl phosphate, hexyl phosphate, cyclohexyl phosphate and benzyl phosphate.

The amount of complexing agent depends on the metal ion content of the reaction medium.

The amount of complexing agent, expressed as the number of moles of complexing agent per mole of hydrogen peroxide, advantageously ranges from 0.0001 to 0.01.

Another embodiment of the process of the invention comprises the hydroxylation of phenolic compounds of formula (I), by means of hydrogen peroxide, in the presence of an effective amount of an alkali metal salt or alkaline earth metal salt of a strong acid and an effective amount of at least one phosphorus oxoacid, in the presence of the keto compound corresponding to the above formula (II).

By "salt of a strong acid" is intended a salt of an acid possessing a pKa in water of less than $-0.1$, and preferably less than $-1.0$.

Among the salts of acids corresponding to this definition, it is preferable to use the alkali metal or alkaline earth metal salts of acids which are stable with respect to oxidation by hydrogen peroxide.

Thus, the alkali metal or alkaline earth metal salts of the strong acids indicated above are completely suitable.

By "alkali metal salts" are intended the neutral lithium, sodium, potassium, rubidium and cesium salts of the acids indicated above.

It is typically preferable to use the sodium or potassium salts, and even more preferably, for economic reasons, the sodium salts.

Among these various salts, preferred are disodium sulfate, sodium perchlorate, sodium trifluoromethanesulfonate, sodium para-toluenesulfonate, sodium chlorosulfonate, sodium fluorosulfonate and sodium methanesulfonate.

By "alkaline earth metal salts" are intended the neutral beryllium, magnesium, calcium, strontium and barium salts of the acids indicated above.

It is typically preferable to use the magnesium, calcium and barium salts.

Among these various alkaline earth metal salts, preferred are calcium sulfate, magnesium sulfate, calcium perchlorate, magnesium perchlorate, calcium trifluoromethanesulfonate, magnesium trifluoromethanesulfonate, calcium fluorosulfonate, magnesium fluorosulphonate, calcium methanesulfonate and magnesium methanesulfonate.

It is possible to use mixtures of a plurality of alkali metal or alkaline earth metal salts.

It is also possible to prepare the alkali metal or alkaline earth metal salts in situ, for example by charging stoichiometric amounts of acid and of oxide or hydroxide of these metals.

The phosphorus oxoacids are, more especially, compounds having an acid function of phosphorus with the oxidation number 5.

It is also possible to use compounds having an acid function of phosphorus with the oxidation number 3, which will be oxidized in the medium by hydrogen peroxide to the corresponding phosphorus V compounds; but this presents no particular advantage while providing the drawback of consuming a fraction of the hydrogen peroxide.

Exemplary such phosphorus V oxoacids include orthophosphoric acid, metaphosphoric acid, pyrophosphoric acid, polyphosphoric acids and phosphonic acids such as (1-hydroxyethylidene)diphosphonic acid, phosphonic acid, ethylphosphonic acid and phenylphosphonic acid.

For practical and economic reasons, those most commonly used are orthophosphoric acid, pyrophosphoric acid and (1-hydroxyethylidene)diphosphonic acid.

The amount of alkali metal salt or alkaline earth metal salt used in the process of the invention can vary over wide limits.

In general, this amount is expressed as the mole ratio of alkali metal salt or alkaline earth metal salt to hydrogen peroxide. This ratio typically ranges from 0.001 to 0.10, and preferably from 0.005 to 0.05.

The amount of phosphorus oxoacid, expressed as the phosphorus oxoacid/hydrogen peroxide mole ratio, typically ranges from 0.001 to 0.20, and preferably from 0.05 to 0.10.

As regards the operating conditions for use of hydrogen peroxide and the keto compound of formula (II), these correspond to that which is described above, as well as that below.

According to the process of the invention, the hydroxylation of the phenolic compound of formula (I) is advantageously carried out at a temperature ranging from 45° C. to 150° C.

In a preferred embodiment of the invention, the temperature ranges from 45° C. to 75° C.

The reaction is advantageously carried out at atmospheric pressure.

The hydroxylation process is generally carried out without a solvent other than that originating from the reactants, such as the solvent of the hydrogen peroxide.

The reaction can, however, also be carried out in a solvent for the phenolic compound (I).

The solvents used must be stable in the presence of hydrogen peroxide.

Non-polar solvents, such as chlorinated aliphatic hydrocarbons, for example dichloromethane, tetrachloromethane and dichloroethane, are representative.

Solvents which are weakly polar such as alcohols and ethers, for example methanol, tert-butanol, isopropanol, ethanol and methyl tert-butyl ether, or highly polar such as water, are also representative.

From a practical standpoint, the process according to the invention is simple to carry out in continuous or discontinuous fashion.

Preferably, the following order of reactants is selected: the phenolic compound of formula (I) is introduced, where appropriate the complexing agent, the strong acid and then the keto compound of formula (II).

The reaction medium is heated to the desired temperature and the hydrogen peroxide solution is added gradually.

Upon completion of the reaction, the unconverted phenolic compound and, where appropriate, the keto compound of formula (II) are separated from the hydroxylation products by standard means, in particular by distillation, and are recycled to the reaction zone.

Exemplary phenolic compounds of formula (I) which may be employed in the process of the invention include phenol, anisole, ortho-cresol, para-cresol, meta-cresol, 4-tert-butylphenol, 2-methoxyphenol and 4-methoxyphenol.

The subject process is especially well suited for the preparation of hydroquinone and pyrocatechol from phenol.

In order to further illustrate the present invention and the advantages thereof, the following specific examples are given, it being understood that same are intended only as illustrative and in nowise limitative.

In said examples to follow, the following abbreviations were used:

$$DC = \frac{\text{number of moles of hydrogen peroxide converted}}{\text{number of moles of hydrogen peroxide introduced}} \%$$

$$CY_{HQ} = \frac{\text{number of moles of hydroquinone formed}}{\text{number of moles of hydrogen peroxide converted}} \%$$

$$CY_{PC} = \frac{\text{number of moles of pyrocatechol formed}}{\text{number of moles of hydrogen peroxide converted}} \%$$

EXAMPLE 1

Comparative Test (a):

A 100-ml glass round-bottomed flask equipped with a central stirrer, a condenser, a dropping funnel and a thermometer was charged with:

(i) 79 g of phenol, (ii) 0.0816 g of trifluoromethanesulfonic acid, (iii) 0.058 g of pyrophosphoric acid, (iv) 3.14 g of benzophenone.

The reaction mixture was heated to 75° C. while maintained under stirring at 1,200 rpm.

2.064 of aqueous hydrogen peroxide solution, 70.5% by weight, were introduced via the dropping funnel over the course of 2 minutes.

The reaction mixture was maintained stirred at 75° C.

The degree of conversion was 100% after 30 minutes.

The reaction mixture was then cooled and an assay of the reaction products was then performed: residual hydrogen peroxide was assayed by iodometry and diphenols formed were assayed by high performance liquid chromatography.

The results obtained were as follows:
$CY$HYDROQUINONE=42.4%
$CY$PYROCATECHOL=41.8%
HQ/PC ratio=1.01

By way of comparison, Example 1 was repeated, in the absence of benzophenone.

The reaction was complete after 1 hour, 50 minutes.

The yields of hydroquinone and pyrocatechol were 34% and 49.6%, respectively, relative to the hydrogen peroxide converted. The ratio of hydroquinone formed to pyrocatechol was 0.685.

It will be seen by comparison of Example 1 and test (a) that the presence of benzophenone influenced the regioselectivity of the reaction and, hence, enabled more hydroquinone to be obtained.

EXAMPLE 2

Comparative Test (b):

A round-bottomed flask as described in Example 1 was charged with:

The amount of reactants introduced and the results obtained are reported in Table I below.

The results obtained using a benzophenone bearing an electron-attracting nitro or cyano group are also reported in Table I.

TABLE 1

HYDROXYLATION OF PHENOL WITH $H_2O_2/H_4P_2O_7/$KETO COMPOUND OF FORMULA (II):

| Example | Keto compound (II) | $H_2O_2$/PHENOL mole ratio | $HClO_4/H_2O_2$ mole ratio | $H_4P_2O_7/H_2O_2$ mole ratio | Keto compound (II)/$H_2O_2$ mole ratio | Time | DC | $CY_{HQ}$ | $CY_{PC}$ | HQ/PC ratio |
|---|---|---|---|---|---|---|---|---|---|---|
| 3 | 4-hydroxy-benzophenone | $5.2 \times 10^{-2}$ | $1.31 \times 10^{-2}$ | $6 \times 10^{-3}$ | 0.670 | 20 min | 100 | 43.0 | 38.0 | 1.13 |
| 4 | 4,4'dihydroxy-benzophenone | $5.1 \times 10^{-2}$ | $1.24 \times 10^{-2}$ | $7 \times 10^{-3}$ | 0.196 | 110 min | 100 | 39.2 | 39.9 | 0.98 |
| 5 | 4,4-diphenyl-benzophenone | $5.1 \times 10^{-2}$ | $1.39 \times 10^{-2}$ | $6 \times 10^{-3}$ | 0.182 | 70 min | 99.9 | 41.3 | 44.4 | 0.93 |
| 6 | 9-fluorenone | $5.0 \times 10^{-2}$ | $1.42 \times 10^{-2}$ | $7 \times 10^{-3}$ | 0.199 | 50 min | 100 | 42.5 | 43.7 | 0.97 |
| 7 | 4-benzoyl-biphenyl | $5.2 \times 10^{-2}$ | $1.25 \times 10^{-2}$ | $7 \times 10^{-3}$ | 0.192 | 75 min | 100 | 41.2 | 42.2 | 0.98 |
| (c) | 4-nitro-benzophenone | $5.3 \times 10^{-2}$ | $1.36 \times 10^{-2}$ | $6 \times 10^{-3}$ | 0.190 | 105 min | 100 | 36.4 | 47.7 | 0.77 |
| (d) | 4-cyano-benzophenone | $4.9 \times 10^{-2}$ | $1.60 \times 10^{-2}$ | $10^{-2}$ | 0.580 | 55 min | 100 | 35.5 | 46.7 | 0.76 |

(i) 30.40 g (0.323 mol) of phenol, (ii) 0.0308 g of aqueous perchloric acid solution, 70% by weight, (iii) 2.18 g of benzophenone, (iv) 0.0161 g of pyrophosphoric acid.

The reaction mixture was heated to 75° C. while maintained under stirring at 1200 rpm.

0.086 g of aqueous hydrogen peroxide solution, 70.5% by weight, was introduced via the dropping funnel over the course of 2 minutes.

The reaction mixture was maintained stirred at 75° C.

The degree of conversion was 100% after 25 minutes.

The reaction mixture was cooled and an assay of the reaction products was performed as in Example 1.

The results obtained were as follows:

$CY$HYDROQUINONE=41.36%

$CY$PYROCATECHOL=43.2%

HQ/PC RATIO=0.96

By way of comparison, Example 2 was repeated, but in the absence of benzophenone.

The reaction was complete after 1 hour.

The yields of hydroquinone and pyrocatechol were 35.2% and 49.6%, respectively, relative to the hydrogen peroxide converted. The ratio of hydroquinone formed to pyrocatechol was 0.71.

EXAMPLES 3 TO 7

Tests (c) and (d):

A series of tests was carried out according to the procedure of Example 2, but employing other keto compounds of formula (II), namely:

4-hydroxybenzophenone (Example 3), 4,4'-dihydroxybenzophenone (Example 4)

4,4'-diphenylbenzophenone (Example 5)

9-fluorenone (Example 6)

4-benzoylbiphenyl (Example 7).

The reaction temperature was 75° C.

It will be seen by examination of Table I that the nature of the group has a surprising influence on the regioselectivity of the reaction, and that only benzophenones bearing an electron-donating group permitted a mixture of hydroquinone and pyrocatechol containing a preponderant amount of hydroquinone to be obtained.

EXAMPLE 8

Test (e):

A 250-ml 3-necked round-bottomed flask equipped with a thermometer, a stirring device, a reflux condenser, a heating system and a nitrogen inlet was charged, after purging with nitrogen, with:

(i) 94 g of molten phenol, (ii) 0.92 g of phosphoric acid, 85% by weight, (iii) 1.82 g of benzophenone, (iv) 1.03 g of aqueous perchloric acid solution, 70% by weight.

The contents of the flask were maintained at 45° C. and 2.02 g of aqueous hydrogen peroxide solution, 84.7% by eight, were then added.

The degree of conversion was 100% after 50 minutes.

The reaction mixture was neutralized with an N/2 solution of potassium hydroxide in methanol, and then diluted by adding one volume of methanol.

The reaction products and the benzophenone were then assayed by gas chromatography. The following results were obtained:

Benzophenone: 1.82 g

Hydroquinone: 2.39 g

Pyrocatechol: 2.33 g

The yields of hydroquinone and pyrocatechol were 42.8% and 41.7%, respectively, relative to the hydrogen peroxide employed. The ratio of hydroquinone formed to pyrocatechol was 1.02.

By way of comparison, Example 8 was repeated, but in the absence of benzophenone.

The degree of conversion was 100% after 3 hours, 12 minutes.

The yields of hydroquinone and pyrocatechol relative to the hydrogen peroxide employed were 33.7% and 52.3%, respectively. The hydroquinone/pyrocatechol ratio was 0.64.

Comparisons of the results of Example 8 and test (e) permits the influence of benzophenone on the distribution of the products formed to be established.

EXAMPLES 9 AND 10

Test (f):

In this series of examples, the amounts of benzophenone introduced were varied according to the data in Table II.

The procedure was that used in Example 8, the operating conditions being as follows:

(i) 1 mol of molten phenol,
(ii) 0.00049 mol of 85% phosphoric acid,
(iii) 0.050 mol of hydrogen peroxide, 84.7% by weight,
(iv) 0.000625 mol of perchloric acid, 70% by weight.

The mole ratios of the reactants were as follows:

$H_2O_2$/phenol mole ratio=$5 \times 10^{-2}$,
$HClO_4/H_2O_2$ mole ratio =$1.25 \times 10^{-2}$,
$H_3PO_4/H_2O_2$ mole ratio=$9.9 \times 10^{-3}$.

Test (f) corresponds to the comparative test with the absence of benzophenone.

The results obtained are repeated in Table II.

TABLE II

Hydroxylation of Phenol with $H_2O_2$/$HClO_4$/$H_3PO_4$/Benzophenone:

| Example | Benzophenone/ $H_2O_2$ mole ratio | Time min | DC | $CY_{HQ}$ | $CY_{PC}$ | HQ/PC ratio |
|---|---|---|---|---|---|---|
| 9 | 0.20 | 30 | 100 | 43.9 | 42.3 | 1.03 |
| 10 | 0.33 | 30 | 100 | 45.0 | 42.0 | 1.06 |
| f | — | 90 | 100 | 35.0 | 50.0 | 0.70 |

EXAMPLE 11

The procedure was as in Example 8, with the reactants and the operating conditions of Examples 9 and 10, but with a benzophenone/$H_2O_2$ mole ratio of 0.5 and an $H_2O_2$/phenol-mole ratio of 0.1.

The degree of conversion was 100% after 30 min.

The results obtained were as follows:
$CY$HYDROQUINONE=37.5%
$CY$PYROCATHECOL=34.8%
HQ/PC ratio=1.07

EXAMPLE 12

The procedure was as in the series of Examples 9 and 10, but replacing benzophenone by 4,4'-dimethylbenzophenone, with an $H_2O_2$/phenol mole ratio of 0.1.

The degree of conversion was 100% after 1 hour.

The results obtained were as follows:
$CY$HYDROQUINONE=40.0%
$CY$PYROCATHECOL=43.6%
HQ/PC ratio=0.92

EXAMPLE 13

The procedure was as in the series of Examples 9 and 10, but replacing benzophenone by 4,4'-dimethylbenzophenone, with an $H_2O_2$/phenol mole ratio of 0.2.

The degree of conversion was 100% after 45 minutes.

The results obtained were as follows:
$CY$HYDROQUINONE=47.2%
$CY$PYROCATHECOL=41.7%
HQ/PC ratio=1.13

EXAMPLE 14

Comparative Test (g):

A 100-ml glass round-bottomed flask equipped with a central stirrer, a condenser, a dropping funnel and a thermometer was charged with:

(i) 41.12 g of phenol,
(ii) 0.081 g of sodium perchlorate $NaClO_4.H_2O$
(iii) 0.236 g of pyrophosphoric acid,
(iv) 0.798 g of benzophenone.

The reaction mixture was heated to 75° C. while maintained under stirring at 1,200 rpm.

1.083 g of aqueous hydrogen peroxide solution, 70.25% by weight, were introduced via the dropping funnel over the course of 2 minutes.

The reaction mixture was maintained stirred at 75° C.

The degree of conversion was 96.1% after 320 minutes.

The reaction mixture was then cooled and an assay of the reaction products was then performed: the residual hydrogen peroxide was assayed by iodometry and the diphenols formed were assayed by high performance liquid chromatography.

The results obtained were as follows:
$CY$HYDROQUINONE=38.0%
$CY$PYROCATHECOL=41.0%
HQ/PC ratio=0.93

By way of comparison, Example 14 was repeated, but in the absence of benzophenone.

The round-bottomed flask as described in Example 14 was charged with:

(i) 41.65 g of phenol,
(ii) 0.078 g of sodium perchlorate $NaClO_4.H_2O$
(iii) 0.221 g of pyrophosphoric acid.

The mixture was heated to 75° C. while maintained under stirring at 1,200 rpm.

1.141 g of aqueous hydrogen peroxide solution, 70.25% by weight, was introduced via the dropping funnel over the course of 2 minutes.

The reaction mixture was maintained stirred at 75° C.

The degree of conversion was 98.6% after 260 minutes.

The reaction mixture was cooled and an assay of the reaction products was performed as in Example 14.

The results obtained were as follows:
$CY$HYDROQUINONE=33.5%
$CY$PYROCATHECOL=50.5%
HQ/PC ratio=0.66

When the results obtained in Example 14 and comparative test (g) were compared, a strong influence of the presence of benzophenone on the regioselectivity of the reaction was noted.

EXAMPLES 15 AND 16

In this series of examples, the influence of temperature on the selectivity of the hydroxylation reaction of phenol to hydroquinone was demonstrated.

The ketone used was benzophenone.

The procedure of Example 1 was repeated, except that perchloric acid was used instead of trifluoromethanesulfonic acid.

The amounts of the reagents and the operating conditions are reported in Table III.

The results obtained are also reported in Table III.

TABLE III

HYDROXYLATION OF PHENOL BY $H_2O_2$/$HClO_4$/$H_4P_2O_7$/BENZOPHENONE:

| Example | Temperature °C. | Molar ratio $H_2O_2$/PHENOL | Molar ratio $HClO_4$/$H_2O_2$ | Molar ratio $H_4P_2O_7$/$H_2O_2$ | Molar ratio benzophenone/$H_2O_2$ | Duration min | DC | $CY_{HQ}$ | $CY_{PC}$ | Ratio HQ/PC |
|---|---|---|---|---|---|---|---|---|---|---|
| 15 | 45 | $5.1 \times 10^{-2}$ | $1.20 \times 10^{-2}$ | $5 \times 10^{-3}$ | 0.20 | 120 | 100 | 42.5 | 41.5 | 1.02 |
| 16 | 75 | $5.2 \times 10^{-2}$ | $1.25 \times 10^{-2}$ | $5 \times 10^{-3}$ | 0.19 | 45 | 100 | 40.1 | 43.3 | 0.93 |

EXAMPLES 17 AND 18

In this series of examples, the influence of acid concentration on the selectivity of the hydroxylation reaction of phenol to hydroquinone was demonstrated.

The ketone used was benzophenone.

The procedure of Example 1 was repeated, except that perchloric acid was used instead of trifluoromethanesulfonic acid.

The amounts of the reagents and the operating conditions are reported in Table IV.

The results obtained are also reported in Table IV.

TABLE IV

HYDROXYLATION OF PHENOL BY $H_2O_2$/$HClO_4$/$H_4P_2O_7$/BENZOPHENONE:

| Example | Temperature °C. | Molar ratio $H_2O_2$/PHENOL | Molar ratio $HClO_4$/$H_2O_2$ | Molar ratio $H_4P_2O_7$/$H_2O_2$ | Molar ratio benzophenone/$H_2O_2$ | Duration min | DC | $CY_{HQ}$ | $CY_{PC}$ | Ratio HQ/PC |
|---|---|---|---|---|---|---|---|---|---|---|
| 17 | 45 | $4.9 \times 10^{-2}$ | $0.4 \times 10^{-2}$ | $6.0 \times 10^{-3}$ | 0.206 | 5 h 45 | 95 | 42.5 | 41.5 | 1.02 |
| 18 | 45 | $5.1 \times 10^{-2}$ | $1.6 \times 10^{-2}$ | $6.0 \times 10^{-3}$ | 0.197 | 2 h | 100 | 43.5 | 48.0 | 0.91 |

EXAMPLE 19

In this example it was demonstrated that the presence of a complexing agent was not necessary if high purity reagents were used.

A phenol marketed by the Carlo Erba Co. having a purity higher than 99.5% was used.

The procedure of Example 1 was repeated, using the following amounts of the reagents:

(i) 0.5 mole of phenol,
(ii) 0.025 mole of benzophenone,
(iii) 0.0244 mole of hydrogen peroxide, 71.2% by weight,
(iv) $3.3 \times 10^{-4}$ mole of perchloric acid, 70% by weight.

The molar ratios of the reagents were as follows:

Molar ratio $H_2O_2$/phenol=$4.9 \times 10^{-2}$,

Molar ratio $HClO_4$/$H_2O_2$=$1.36 \times 10^{-2}$,

Molar ratio benzophenone/$H_2O_2$=1.03.

The results obtained are reported in Table V.

TABLE V

HYDROXYLATION OF PHENOL BY $H_2O_2$/$HClO_4$/BENZOPHENONE:

| Example | Temperature | Duration min | DC | $CY^{HQ}$ | $CY^{PC}$ | HQ/PC |
|---|---|---|---|---|---|---|
| 19 | 75 | 30 | 100 | 42.5 | 42.0 | 1.01 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxylation of a phenolic compound having the formula (I):

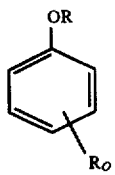

(I)

in which R and $R_0$, which are identical or different, are each a hydrogen atom, an alkyl radical having from 1 to 4 carbon atoms, a cyclohexyl radical or a phenyl radical, comprising reacting such phenolic compound with hydrogen peroxide in the presence of an effective amount of a strong acid and a catalytically effective amount of a keto compound having the formula (II):

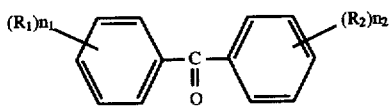

(II)

wherein $R_1$ and $R_2$, which are identical or different, are each a hydrogen atom or an electron-donating group; $n_1$ and $n_2$, which are identical or different, are numbers equal to 0, 1, 2 or 3, with the proviso that the two carbon atoms located at the α-position with respect to the two carbon atoms bearing the —CO— group are optionally bonded together via a valence bond or via a —$CH_2$— group, thereby forming a keto-containing ring member which is saturated or unsaturated.

2. The process as defined by claim 1, wherein formula (II), $R_1$ and $R_2$, which are identical or different, are each:

(a) a linear or branched alkyl radical having from to 4 carbon atoms;

(b) a phenyl radical;

(c) an alkoxy radical $R_3$—O— in which $R_3$ is a linear or branched alkyl radical having from 1 to 4 carbon atoms or a phenyl radical;

(d) a hydroxyl group; or (e) a fluorine atom.

3. The process as defined by claim 1, wherein formula (II), $R_1$ and $R_2$, which are identical or different, are each a hydrogen atom or an electron-donating group at the 4,4'-position and $n_1$ and $n_2$, which are identical or different, are equal to 0 or 1.

4. The process as defined by claim 1, wherein formula (II), $R_1$ and $R_2$, which are identical or different, are each: a hydrogen atom; a methyl radical; an ethyl radical; a tert-butyl radical; a phenyl radical; a methoxy radical; an ethoxy radical; or a hydroxyl group.

5. The process as defined by claim 1, wherein said keto compound of formula (II) is benzophenone, 2-methylbenzophenone, 2,4-dimethylbenzophenone, 4,4'-dimethylbenzophenone, 2,2'-dimethylbenzophenone, 4,4'-dimethoxybenzophenone, fluorenone, 4-hydroxybenzophenone, 4,4'-dihydroxybenzophenone or 4-benzoylbiphenyl.

6. The process as defined by claim 1, wherein the amount of keto compound of formula (II) is at least $1 \times 10^{-3}$ mole per mole of hydrogen peroxide.

7. The process as defined by claim 1, wherein said strong acid has a pKa in water of less than −0.1.

8. The process as defined by claim 1, wherein said strong acid is sulfuric acid, pyrosulfuric acid, perchloric acid, nitric acid, fluorosulfonic acid, chlorosulfonic acid, trifluoromethanesulfonic acid, methanesulfonic acid, ethanesulfonic acid, ethanedisulfonic acid, benzenesulfonic acid, a benzenedisulfonic acid, a toluenesulfonic acid, a naphthalenesulfonic acid or a naphthalenedisulfonic acid.

9. The process as defined by claim 8, wherein said strong acid is perchloric acid or trifluoromethanesulfonic acid.

10. The process as defined by claim 1, wherein the amount of strong acid is such that the $H^+/H_2O_2$ ratio ranges from $1 \times 10^{-4}$ to 1.0.

11. The process as defined by claim 1, wherein the mole ratio of $H_2O_2$ to phenolic compound of formula (I) ranges from 0.01 to 0.3.

12. The process as defined by claim 1, further comprising carrying out said process in the presence of an agent which complexes transition metal ions and which is stable under the conditions of the reaction.

13. The process as defined by claim 1, wherein said process is carried out at a temperature ranging from 45° C. to 150° C.

14. The process as defined by claim 1, wherein said phenolic compound of formula (I) is phenol, anisole, ortho-cresol, para-cresol, meta-cresol, 4-tert-butylphenol, 2-methoxyphenol or 4-methoxyphenol.

15. The process as defined by claim 14, wherein said phenolic compound of formula (I) is phenol.

16. A process for the hydroxylation of a phenolic compound having the formula (I):

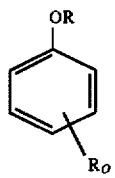

in which R and $R_0$, which are identical or different, are each a hydrogen atom, an alkyl radical having from 1 to 4 carbon atoms, a cyclohexyl radical or a phenyl radical, comprising reacting such phenolic compound with hydrogen peroxide in the presence of an alkali metal salt or alkali earth metal salt of a strong acid and a catalytically effective amount of at least one phosphorous oxoacid, in the presence of a keto compound having the formula (II):

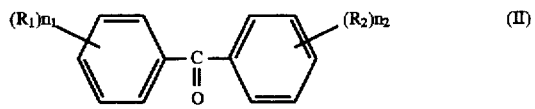

wherein $R_1$ and $R_2$, which are identical or different, are each a hydrogen atom or an electron-donating group; $n_1$ and $n_2$, which may be identical or different, are numbers equal to 0, 1, 2 or 3, with the proviso that the two carbon atoms located at the α-position with respect to the two carbon atoms bearing the —CO group are optionally bonded together via a valence bond or via a —$CH_2$— group, thereby forming a keto-containing ring member which is saturated or unsaturated.

17. The process as defined by claim 16, wherein said process is carried out in the presence of an effective amount of said alkali metal salt or alkaline earth metal salt of a strong acid.

18. The process as defined by claim 16, wherein said alkali metal salt or alkaline earth metal salt of a strong acid is a salt of sulfuric acid, pyrosulfuric acid, perchloric acid, nitric acid, fluorosulfonic acid, chlorosulfonic acid, trifluoromethanesulfonic acid, methanesulfonic acid, ethanesulfonic acid, ethanedisulphonic acid, benzenesulfonic acid, a benzenedisulfonic acid, a toluenesulfonic acid, a naphthalenesulfonic acid or a naphthalenedisulfonic acid.

19. The process as defined by claim 16, wherein said alkali metal salt or alkali earth metal salt is disodium sulfate, sodium perchlorate, sodium trifluoromethanesulfonate, sodium para-toluenesulfonate, sodium chlorosulfonate, sodium fluorosulfonate or sodium methanesulfonate.

20. The process as defined by claim 16, wherein said alkali metal salt or alkali earth metal salt is calcium sulfate, magnesium sulfate, calcium perchlorate, magnesium perchlorate, calcium trifluoromethanesulfonate, magnesium trifluoromethanesulfonate, calcium para-toluenesulfonate, magnesium para-toluenesulfonate, calcium fluorosulfonate, magnesium fluorosulfonate, calcium methanesulfonate or magnesium methanesulfonate.

21. The process as defined by claim 17, wherein said at least one phosphorus oxoacid has an acid function of phosphorus with the oxidation number 5.

22. The process as defined by claim 21, wherein said phosphorus oxoacid is orthophosphoric acid, metaphosphoric acid, pyrophosphoric acid, a polyphosphoric acid or a phosphortic acid.

23. The process as defined by claim 21, wherein said at least one phosphorus oxoacid is orthophosphoric acid, pyrophosphoric acid or (1-hydroxy-ethylidene)diphosphonic acid.

24. The process as defined by claim 16, wherein the amount of alkali metal salt or akaline earth metal salt, expressed as the mole ratio of alkali metal salt or alkaline earth metal salt to hydrogen peroxide, ranges from 0.001 to 0.10.

25. The process as defined by claim 16, wherein the amount of phosphorus oxoacid, expressed as the phosphorus oxoacid/hydrogen peroxide mole ratio, ranges from 0.001 to 0.20.

26. The process as defined by claim 16, wherein the mole ratio of $H_2O_2$ to phenolic compound of formula (I) ranges from 0.01 to 0.3.

27. The process as defined by claim 16, wherein said process is carried out at a temperature ranging from 45° C. to 150° C.

28. The process as defined by claim 16, wherein said phenolic compound of formula (I) is phenol, anisole, ortho-cresol, para-cresol, meta-cresol, 4-tert-butylphenol, 2-methoxyphenol or 4-methoxyphenol.

29. The process as defined by claim 16, wherein said phenolic compound of formula (I) is phenol.

30. The process as defined by claim 16, wherein formula (II), $R_1$ and $R_2$, which are identical or different, are each:
  (a) a linear or branched alkyl radical having from 1 to 4 carbon atoms;
  (b) a phenyl radical;
  (c) an alkoxy radical $R_3$—O— in which $R_3$ is a linear or branched alkyl radical having from 1 to 4 carbon atoms or a phenyl radical;
  (d) a hydroxyl group; or
  (e) a fluorine atom.

31. The process as defined by claim 16, wherein formula (II), $R_1$ and $R_2$, which are identical or different, are each a hydrogen atom or an electron-donating group at the 4,4'-position and $n_1$ and $n_2$, which are identical or different, are equal to 0 or 1.

32. The process as defined by claim 16, wherein formula (II), $R_1$ and $R_2$, which are identical or different, are each: a hydrogen atom; a methyl radical; an ethyl radical; a tert-butyl radical; a phenyl radical; a methoxy radical; an ethoxy radical; or a hydroxyl group.

33. The process as defined by claim 16, wherein said keto compound of formula (II) is benzophenone, 2-methylbenzophenone, 2,4-dimethylbenzophenone, 4,4'-dimethylbenzophenone, 2,2'-dimethylbenzophenone, 4,4'-dimethoxybenzophenone, fluorenone, 4-hydroxybenzophenone, 4,4'-dihydroxybenzophenone or 4-benzoylbiphenyl.

34. The process as defined by claim 16, wherein the amount of keto compound of formula (II) is at least $1 \times 10^{-3}$ mole per mole of hydrogen peroxide.

* * * * *